United States Patent [19]

Hojo et al.

[11] Patent Number: 4,855,501

[45] Date of Patent: Aug. 8, 1989

[54] PROCESS FOR PREPARATION OF MONOMETHYLHYDRAZINE

[75] Inventors: Shiro Hojo, Sakaide; Yoichi Hasegawa; Takeo Hirai, both of Marugame, all of Japan

[73] Assignee: Japan Hydrazine Co., Inc., Tokyo, Japan

[21] Appl. No.: 327,088

[22] Filed: Dec. 3, 1981

[30] Foreign Application Priority Data

Dec. 10, 1980 [JP] Japan .................. 55-173116

[51] Int. Cl.$^4$ .......................... C07C 109/04
[52] U.S. Cl. ................................ 564/314
[58] Field of Search .................. 564/313, 464

[56] References Cited

U.S. PATENT DOCUMENTS

| | | | |
|---|---|---|---|
| 3,083,229 | 3/1963 | Oja | 564/464 |
| 3,140,315 | 7/1964 | Klos et al. | 564/464 X |
| 4,124,452 | 11/1978 | Henderson | 564/464 X |
| 4,281,198 | 7/1981 | Hojo et al. | 564/464 |

FOREIGN PATENT DOCUMENTS 875152  8/1961  United Kingdom ............... 564/313

OTHER PUBLICATIONS

Kirk-Othmer, "Encyclopedia of Chemical Technology", vol. 11, 2nd Ed, pp. 168 and 173–174 (1966).

*Primary Examiner*—Robert V. Hines
*Attorney, Agent, or Firm*—Sherman and Shalloway

[57] ABSTRACT

Disclosed is a process for the preparation of monomethylhydrazine which comprises reacting hydrazine monohydrochloride with methanol in the presence of hydrazine dihydrochloride or methyl chloride and recovering free monomethylhydrazine from the formed monomethylhydrazine hydrochloride.

According to this process, monomethylhydrazine can be prepared at a high selectivity very easily while controlling formation of by-products.

8 Claims, No Drawings

PROCESS FOR PREPARATION OF MONOMETHYLHYDRAZINE

BACKGROUND OF THE INVENTION

1. Field of the Invention:

The present invention relates to a novel process for the preparation of monomethylhydrazine. More particularly, the present invention relates to a process for the preparation of monomethylhydrazine which comprises reacting under heating hydrazine monohydrochloride with methanol in the presence of hydrazine dihydrochloride or methyl chloride.

2. Description of the Prior Art:

Monomethylhydrazine (hereinafter referred to as "MMH") is a very valuable compound which is widely used in the industries of pharmaceuticals and agricultural chemicals, the chemical industries, the aerospace and missile industries and other various industries.

As the process for the preparation of MMH, there are known so-called modified Raschig's processes such as a process comprising reacting monomethylamine with chloroamine obtained by reacting ammonia with sodium hypochlorite and a process comprising reacting monomethylurea and sodium hypochlorite with sodium hydroxide. These processes are not satisfactory from the industrial viewpoint, because the yield of MMH is low and the concentration of formed MMH in the reaction mixture liquid is low to render the purification step complicate and increase the manufacturing cost. It also is known that alkylhydrazines are formed by reaction of alkyl halides with hydrazine. However, when hydrazine is reacted with a methyl halide, by-products such as assymetric dimethylhydrazine, symmetric dimethylhydrazine and trimethylhydrazinium halide are formed in addition to intended MMH. Accordingly, the step of separating the intended product is complicated and the yield is low. Therefore, this process has not been carried out on an industrial scale.

SUMMARY OF THE INVENTION

We made researches on the industrial process for preparing MMH from hydrazine, and we found that when methyl chloride or hydrazine dihydrochloride is added as a catalyst to a mixed liquid of hydrazine monohydrochloride and methanol and reaction is carried out under heating, MMH can be formed at a high selectivity. The present invention has now been completed based on this finding.

More specifically, in accordance with the present invention, there is provided a process for the preparation of monomethylhydrazine which comprises reacting hydrazine monohydrochloride with methanol in the presence of hydrazine dihydrochloride or methyl chloride and recovering free monomethyl hydrazine from the formed monomethylhydrazine hydrochloride.

DETAILED DESCRIPTION OF THE PREFERRED EMBODIMENTS

The reaction mechanism of the present invention has not completely been elucidated, but it is believed that the reaction will probably be advanced as shown below.

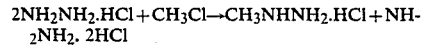

$$2NH_2NH_2 \cdot HCl + CH_3Cl \rightarrow CH_3NHNH_2 \cdot HCl + NH_2NH_2 \cdot 2HCl \quad (1)$$

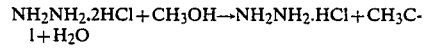

$$NH_2NH_2 \cdot 2HCl + CH_3OH \rightarrow NH_2NH_2 \cdot HCl + CH_3Cl + H_2O \quad (2)$$

As is seen from the above reference formulae, according to the process of the present invention, MMH can be obtained very easily at a high selectively from hydrazine monohydrochloride and methanol which are industrially manfactured in large quantities. Accordingly, the process of the present invention is very advantageous from the economical viewpoint.

In the present invention, hydrazine monhydrochloride may be used in the solid form or in the form of an aqueous solution. From the economical viewpoint, it is preferred that an aqueous solution of hydrazine monohydrochloride obtained by adding a concentrated aqueous solution of hydrochloric acid to hydrazine hydrate is used. Methyl chloride which is used as the catalyst may be fed to the reaction system directly or in the form of a solution in methanol. Hydrazine dihydrochloride may be used in the solid form or in the form of a solution in water or methanol. Instead of a method in which hydrazine dihydrochloride as the catalyst is added independently to the reaction system, there may be adopted a method in which hydrazine dihydrochloride is formed in situ by adding hydrochloric acid to the starting hydrazine monohydrochloride solution or the reaction mixture. Methyl chloride recovered by means described hereinafter may be recycled and used repeatedly.

In the present invention, the reaction is carried out at a temperature of 90 to 140°C. preferably 110 to 130°C.

The molar ratio of hydrazine monohydrochloride to methanol is preferably in the range of from 1/1 to 1/6 and especially preferably in the range of from ½ to 1/5.

It is preferred that methyl chloride or hydrazine dihydrochloride is used in an amount of 5 to 20 mole % based on hydrazine monohydrochloride.

The reaction pressure is changed according to the amount of the catalyst, the amount of methanol and the reaction temperature, but a pressure spontaneously generated at the above reaction temperature is ordinarily sufficient. It is usually preferred that the reaction is carried out under a pressure of 7 to 13 Kg/cm².

The reaction time is preferably in the range of 0.5 to 2 hours. If the reaction time is too long, the selectivity is reduced. The process of the present invention may be carried out in a continuous manner or batchwise.

The reaction mixture liquid obtained according to the present invention is subjected to distillation, whereby the majorities of methanol and methyl chloride as the catalyst can be recovered. Since the thus recovered methyl chloride-containing methanol can be recycled and used for the reaction repeatedly, the loss of the catalyst can be reduced to a very low level. Another prominent advantage of the present invention is that the methanol solubilities of MMH hydrochloride and hydrazine monohydrochloride are greatly different from each other even at temperatures approximating room temperature. Namely, the methanol solubility of MMH hydrochloride is much higher than the methanol solubility of hydrazine monohydrochloride. Accordingly, crystals of hydrazine monohydrochloride cna be separated from the methanol solution containing MMH hydrochloride. Separated hydrazine monohydrochloride can be recycled and used for the reaction repeatedly. An aqueous solution of an alkali is added to the liquid reaction mixture left after hydrazine monohydrochloride has been separated, whereby methylhydrazine is set free. Accordingly, pure methylhydrazine can be recovered by then conducting rectification.

The process of the present invention will now be described in detail with reference to the following Examples that by no means limit the scope of the invention.

EXAMPLE 1

A glass-lined autoclave was charged with 68.5 g (1 mole) of crystalline hydrazine monohydrochloride, 160 g (5 moles) of methanol and 7.58 g (0.15 mole) of methyl chloride, and reaction was carried out at 130°C. under a pressure of 12 Kg/cm$^2$ for 2 hours. After completion of the reaction, about 4 moles of methanol was recovered by distillation, and the residual liquid reaction mixture was analyzed. The obtained results are as follows:
Converion of hydrazine monohydrochloride: 29.7%
Selectivity to MMH: 99.9%
Selectivity to 1,1-dimethylhydrazine: 0.1%
Selectivity to 1,1,2-trimethylhydrazine: 0%
Selectivity to 1,2-dimethylhydrazine: 0%
Ratio of recovery of methyl chloride in methanol: 99.3%

EXAMPLE 2

A glass-lined autoclave was charged with 68.5 g (1 mole) of hydrazine monohydrochloride, 160 g (5 moles) of methanol and 15.75 g (0.15 mole) of hydrazine dihydrochloride, and reaction was carried out at 125°C. under a pressure of 12 Kg/cm$^2$ for 2 hours. The obtained results are as follows:
Conversion of hydrazine monohydrochloride: 22.0%
Selectivity to MMH: 99.0%
Selectivity to 1,1-dimethylhydrazine: 1.0%
Selectivity to 1,2-dimethylhydrazine: 0%

EXAMPLE 3

A glass-lines autoclave was charged with 137 g (1 mole) of a 50% aqueous solution of hydrazine monohydrochloride, 96 g (3 moles) of methanol and 5.05 g (0.1 mole) of methyl chloride, and reaction was carried out at 130° C. under a pressure of 10 Kg/cm$^2$ for 1 hours. The obtained liquid reaction mixture was analyzed to obtain the following results:
Conversion of hydrazine monohydrochloride: 22.0%
Selectivity to MMH: 99.8%
Selectivity to 1,1-dimethylhydrazine: 0.2%
Selectivity to 1,2-dimethylhydrazine: 0%
Selectivity to 1,1,1-trimethylhydrazine: 0%

EXAMPLE 4

A glass autoclave was charged with 137 g (1 mole) of a 50% aqueous solution of hydrazine monohydrochloride, 64 g (2 moles) of methanol and 10.1 g (0.2 mole) of methyl chloride, and reaction was carried out at 90°C. under a pressure of 7.2 Kg/cm$^2$ for 3 hours. The liquid reaction mixture was withdrawn and analyzed to obtain the following results:
Conversion of hydrazine monohydrochloride: 13.3%
Selectivity to monomethylhydrazine: 96.2%
Selectivity to 1,1-dimethylhydrazine: 3.7%

EXAMPLE 5

A glass autoclave was charged with 137 g (1 mole) of a 50% aqueous solution of hydrazine monohydrochloride, 64 g (2 moles) of methanol and 10.1 g (0.2 mole) of methyl chloride, and reaction was carried out at 100°C. under a pressure of 8 Kg/cm$^2$ for 30 minutes. The liquid reaction mixture was withdrawn and analyzed to obtain the following results:
Conversion of hydrazine monohydrochloride: 8.0%
Selectivity to monomethylhydrazine: 98.0%
Selectivity to 1,1-dimethylhydrazine: 1/8%

EXAMPLE 6

A glass-lined autoclave was charged with 68.5 g (1 mole) of hydrazine monohydrochloride, 64 g (2 moles) of methanol and 15.75 g (0.15 mole) of hydrazine dihydrochloride, and reaction was carried out at 120°C. under a pressure of 9 Kg/cm$^2$ for 40 minutes. THe liquid reaction mixture was analyzed to obtain the following results:
Conversion to hydrazine monohydrochloride: 20.2%
Selectivity to MMH: 99.&%
Selectivity to 1,2-dimethylhydrazine: trace
Selectivity to 1,1,1-trimethylhydrazine: 0%

EXAMPLE 7

A glass-lined autoclave was charged with 68.5 g (1 mole) of hydrazine monohydrochloride, 64 g (2 moles) of methanol and 15.75 g (0.15 mole) of hydrazine dihydrochloride, and reaction was carried out at 110°C. under a pressure of 8 Kg/cm$^2$ for 2 hours. The liquid reaction mixture was analyzed to obtain the following results:
Conversion of hydrazine monohydrochloride: 15%
Selectivity to MMH: 99.9%
Selectivity to 1,1-dimethylhydrazine: 0.1%
Selectivity to 1,2-dimethylhudrazine: 0%
Selectivity to 1,1,1-trimethylhydrazine: 0%

EXAMPLE 8

A glass-lined autoclave was charged with 68.5 g (1 mole) of hydrazine monohydrochloride, 96 g (3 moles) of methanol and 5.25 g (0.05 mole) of hydrazine dihydrochloride, and reaction was carried out at 130°C. under a pressure of 12 Kg/cm$^2$ for 2 hours. The liquid reaction mixture was analyzed to obtain the following results:
Conversion of hydrazine monohydrochloride: 15%
Selectivity to MMH: 100%
Selectivity to other methylhydrazines: 0%

EXAMPLE 9

A glass-lined autoclave was charged with 137 g (1 mole) of a 50% aqueous solution of hydrazine monohydrochloride, 128 g (4 moles) of methanol and 21 g (0.2 mole) of hydrazine dihydrchloride, and reaction was carried out at 125°C. under a pressure of 12 Kg/cm$^2$ for 60 minutes. The liquid reaction mixture was analyzed to obtain the following results:
Conversion of hydrazine monohydrochloride: 23%
Selectivity to MMH: 99.9%
Selectivity to 1,1-dimethylhydrazine: 0.1%
Selectivity to 1,2-dimethylhydrazine: 0%
Selectivity to 1,1,1-trimethylhydrazine: 0%

EXAMPLE 10

A 50% aqueous solution of hydrazine monohydrochloride and a methanol solution containing 5.5% by weight of methyl chloride dissolved therein were fed severally to a 40A glass-lined double-tube reactor having a length of 2 m and inner capacity of 2.2 liters, at rates of 718.8 g/hr and 814 g/hr, respectively, through preheating tubes for heating both the solutions up to 100°C., by high pressure pumps. In the reactor, reaction was carried out at 130°C. under a pressure of 12 to 13

Kg/cm² for 24 hours. Other reaction conditions were as follows:

Residence time: 1.37 hours

Methanol/hydrazine monohydrochloride molar ratio: 4.6

Methyl chloride/hydrazine monohydrochloride molar ratio: 0.17

The obtained liquid reaction mixture was analyzed to obtain the following results:

Conversion of hydrazine monohydrochloride: 22.5%

Selectivity to MMH: 97.9%

Selectivity to 1,1-dimethylhydrazine: 2.1%

Selectivity to 1,2-dimethylhydrazine: 0%

Selectivity to 1,1,1-trimethylhydrazine: 0%

Then, the liquid reaction mixture was subjected to distillation to remove methanol and water therefrom, and methanol was added to the residue to dissolve the hydrochloride of MMH therein. Hydrazine monohydrochloride was separated as the crystal by centrifugal separation, and sodium hydroxide was added to the obtained methanol solution to effect neutralization. The mxiture was subjected to rectification to obtain MMH at a recovery ratio of 96% (based on MMH contained in the liquid reaction mixture). Furthermore, 1,1-dimethylhydrazine was obtained at a recovery ratio of 95%.

What is claimed is:

1. A process for the preparation of monomethylhydrazine which comprises reacting hydrazine monohydrochloride with methanol in the presence of a catalytic amount of hydrazine dihydrochloride or methyl chloride and recovering free monomethyl hydrazine from the formed monomethylhydrazine hydrochloride.

2. A process according to claim 1, wherein methyl chloride or hydrazine dihydrochloride is made presetn in an amount of 5 to 20 mole % based on hydrazine monohydrochloride.

3. A process according to claim 1, wherein hydrazine monohydrochloride and methanol are made present at a molar ratio of from 1/1 to 1/6.

4. A process according to claim 1, wherein the reaction is carried out at a temperature of 90 to 140C.

5. A process according to claim 1, wherein the formed reaction mixture is subjected to distillation to remove excessive methylchloride, methanol and water, and then the distillation residue containing monomethylhydrazine hydrochloride is fed into methanol, and deposited unreacted hydrazine monohydrochloride is separated out in the form of crystal from the above methanol solution, and remained monomethylhydrazine hydrochloride methanol solution is neutralized with an alkali and then is subjected to fractional distillation to obtain monomethylhydrazine.

6. A process according to claim 3 wherein the molar ratio is from ½ to 1/5.

7. A process according to claim 4 wherein the temperature is from 110° to 130°C.

8. A process according to claim 2 wherein hydrazine monohydrochloride and methanol are made present at a molar ratio of from 1/1 to 1/6 and wherein the reaction is carried out at a temperature of 90° to 140°C. uner pressure of 7 to 13 kg/cm² for a period of from 0.5 to 2 hours.

* * * * *

UNITED STATES PATENT AND TRADEMARK OFFICE
CERTIFICATE OF CORRECTION

PATENT NO. : 4,855,501

DATED : August 8, 1989

INVENTOR(S) : SHIRO HOJO ET AL.

It is certified that error appears in the above-identified patent and that said Letters Patent is hereby corrected as shown below:

Claim 2, line 2 of the claim, "presetn" should read --present--.

Claim 4, line 2 of the claim, "140C" should read --140°C--.

Claim 8, line 4 of the claim, "uner" should read --under--.

Signed and Sealed this

Twelfth Day of June, 1990

Attest:

HARRY F. MANBECK, JR.

*Attesting Officer*      *Commissioner of Patents and Trademarks*